(12) United States Patent
Lee et al.

(10) Patent No.: US 10,316,319 B2
(45) Date of Patent: Jun. 11, 2019

(54) COMPOSITION FOR DIAGNOSIS OF LIVER METASTASIS OF COLORECTAL CANCER AND THE USE THEREOF

(71) Applicant: SAMSUNG LIFE PUBLIC WELFARE FOUNDATION, Seoul (KR)

(72) Inventors: Woo Yong Lee, Seoul (KR); Yong Beom Cho, Seoul (KR); Ho-Kyung Chun, Seoul (KR)

(73) Assignee: SAMSUNG LIFE PUBLIC WELFARE FOUNDATION, Seoul (KR)

(*) Notice: Subject to any disclaimer, the term of this patent is extended or adjusted under 35 U.S.C. 154(b) by 129 days.

(21) Appl. No.: 15/347,386

(22) Filed: Nov. 9, 2016

(65) Prior Publication Data

US 2017/0218373 A1   Aug. 3, 2017

Related U.S. Application Data

(63) Continuation-in-part of application No. 13/217,225, filed on Aug. 24, 2011, now abandoned.

(30) Foreign Application Priority Data

Dec. 16, 2010 (KR) .................. 10-2010-0129207

(51) Int. Cl.
| | | |
|---|---|---|
| *C07H 21/02* | (2006.01) | |
| *C07H 21/04* | (2006.01) | |
| *A61K 48/00* | (2006.01) | |
| *C12N 15/113* | (2010.01) | |
| *C07K 16/24* | (2006.01) | |
| *A61K 31/216* | (2006.01) | |
| *C12Q 1/6886* | (2018.01) | |
| *G01N 33/574* | (2006.01) | |

(52) U.S. Cl.
CPC ........ *C12N 15/1135* (2013.01); *A61K 31/216* (2013.01); *C07K 16/24* (2013.01); *C12Q 1/6886* (2013.01); *G01N 33/57419* (2013.01); *G01N 33/57438* (2013.01); *C07K 2317/76* (2013.01); *C12N 2310/14* (2013.01); *C12Q 2600/118* (2013.01); *C12Q 2600/158* (2013.01); *G01N 2333/7158* (2013.01)

(58) Field of Classification Search
CPC .... A61K 31/713; C12N 15/111; C12N 15/113
See application file for complete search history.

(56) References Cited

PUBLICATIONS

Aagaard, L., et al., (2007). "RNAi therapeutics: principles, prospects and challenges". *Advanced Drug Delivery Reviews*. 59(2-3):75-86.

Cho, Y.B., (2010). "Chemokine (c-c motif) ligand 7 expression in liver metastasis of colorectal cancer."

Clackson, T., et al., (1991). "Making antibody fragments using phage display libraries" *Letters to Nature*. 352:624-628.

Heng, H.H.Q., et al., (2009). "Genetic and epigenetic heterogeneity in cancer: a genome-centric perspective". *Journal of Cellular Physiology*. 220:538-547.

Jung, D.-W. et al., (2010). "Tumor-stromal crosstalk in invasion of oral squamous cell carcinoma: a pivotal role of ccl7". *International Journal of Cancer*. 127:332-344.

Ki, D.H., et al., (2007). "Whole genome analysis for liver metastasis gene signatures in colorectal cancer". *Int. J. Cancer*. 121:2005-2012.

Kohler, G., et al. (1976). "Derivation of specific antibody-producing tissue culture and tumor lines by cell fusion" *European Journal of Immunology*. 6(7):511-519.

Marks, J.D. et al., (1991). "By-passing immunization: human antibodies from v-gene libraries displayed on phage". *Journal of Molecular Biology*. 222:581-597.

Wang, J.M. , et. al., (1998). "Chemokines and their role in tumor growth and metastasis". *Journal of Immunological Methods*. 220:1-17.

Office Action (Non-final) dated May 16, 2016 issued in U.S. Appl. No. 13/217,225.

Office Action (Final) dated May 7, 2015 issued in U.S. Appl. No. 13/217,225.

Office Action (Non-final) dated Dec. 15, 2014 issued in U.S. Appl. No. 13/217,225.

Office Action (Final) dated Jul. 30, 2013 issued in U.S. Appl. No. 13/217,225.

Office Action (Non-Final) dated Mar. 28, 2013 issued in U.S. Appl. No. 13/217,225.

Office Action (Restriction Requirement) dated Feb. 7, 2013 issued in U.S. Appl. No. 13/217,225.

Office Action (Restriction Requirement) dated Nov. 2, 2012 issued in U.S. Appl. No. 13/217,225.

*Primary Examiner* — Amy H Bowman
(74) *Attorney, Agent, or Firm* — Harness, Dickey & Pierce, P.L.C.

(57) ABSTRACT

The present disclosure relates to a composition for diagnosis of liver metastasis of colorectal cancer and the use thereof, and more particularly to a composition for diagnosis of liver metastasis of colorectal cancer, which comprises either a substance for measuring the mRNA level of CCL7 (Chemokine (C-C motif) ligand 7) gene or a substance for measuring the level of a protein which is encoded by the gene. According to the present disclosure, whether liver metastasis of colorectal cancer occurred can be diagnosed by measuring the mRNA expression level of the CCL7 gene or the expression level of the CCL7 protein, and the use of the composition comprising an inhibitor of CCL7 gene allows the treatment of colorectal cancer or the liver metastasis of colorectal cancer.

5 Claims, 10 Drawing Sheets
Specification includes a Sequence Listing.

COMPOSITION FOR DIAGNOSIS OF LIVER METASTASIS OF COLORECTAL CANCER AND THE USE THEREOF

CROSS-REFERENCE TO RELATED APPLICATIONS

This application is a continuation-in-part application of Ser. No. 13/217,225, filed Aug. 24, 2011, which claims benefit of Korean Patent Application No. 10-2010-0129207, filed on Dec. 16, 2010. The entire disclosures of the applications identified in this paragraph are incorporated herein by references.

FIELD

The present disclosure relates to a composition for diagnosis and treatment of liver metastasis of colorectal cancer and the use thereof, and more particularly to a composition for diagnosis of liver metastasis of colorectal cancer, which comprises a substance for measuring the mRNA level of CCL7 (Chemokine (C-C motif) ligand 7) gene or a substance for measuring the level of a protein which is encoded by the gene.

BACKGROUND

Colorectal cancer is the third most common cancer in the world. In Korea, colorectal cancer is the fourth most common cancer after stomach, lung and liver cancers in men, and is the third most common cancer after breast and stomach cancers in women. Recently, as Korean eating habits have become westernized, the incidence of colorectal cancer has increased rapidly in Korea. During recent 10 years in Korea, the mortality caused by colorectal cancer has increased by about 80% and showed a tendency to increase gradually (Korean Central Cancer Registry 2002). About 50% patients with colorectal cancer die within 5 years after diagnosis, and 15-25% of the patients are found to have liver metastasis at the time of diagnosis, and 20-30% of the patients are found to have liver metastasis during follow-up observation after surgery of primary colorectal cancer. Indeed, the cause of death of patients with malignant tumors, including colorectal cancer, is due to the metastasis of malignant tumors rather than the malignant tumors themselves.

Cancer-related studies have mostly been conducted on carcinogenic processes and mechanisms. In order to improve the treatment and survival rate of colorectal cancer patients, studies on colorectal cancer metastasis which is the most common cause of death are required, and among them, studies on the metastasis of colorectal cancer to the liver that is the most common metastasis site are necessary.

In many studies conducted to date, a microarray gene expression profiling technique has been used to discover biomarkers related to the occurrence or metastasis of malignant tumors. Although this technique allows the expression of whole genes to be determined, it is difficult to carry out, is very expensive and has high false-positivity. Also, additional processes of examining the expression levels of genes by Northern blotting, RT-PCR and the like should be performed after the test. The $RT^2$ Profiler PCR Array comprises a 96-well plate containing SYBR Green-optimized primer sets for genes classified according to pathway (e.g., apoptosis, cell cycle, cancer, signal pathway, etc.) or disease and can analyze the expression of a group of groups involved in a specific signal pathway using a real time PCR-based technique.

Accordingly, the present inventors have made extensive efforts to develop a biomarker capable of diagnosing the liver metastasis of colorectal cancer and, as a result, have found that, when the mRNA expression level of CCL7 gene and the level of CCL7 protein are compared between the liver metastasis site of colorectal cancer and the primary site of colorectal cancer, the mRNA level of the CCL7 gene is more strongly expressed at the liver metastasis site and the level of the CCL7 protein is also higher at the liver metastasis site, suggesting that the CCL7 gene can be used as a biomarker specific for liver metastasis of colorectal cancer, thereby completing the present invention.

SUMMARY

The present disclosure provides a composition for diagnosis and treatment of liver metastasis of colorectal cancer, which comprises either a substance for measuring the mRNA level of CCL7 (Chemokine (C-C motif) ligand 7) gene or a substance for measuring the level of a protein which is encoded by the gene, and a kit for diagnosis of liver metastasis of colorectal cancer, which comprises the composition.

In another embodiment, the present disclosure provides a composition for inhibiting liver metastasis of colorectal cancer, which comprises an inhibitor of CCL7 (Chemokine (C-C motif) ligand 7) gene, or the CCL7 signaling pathway.

In yet another embodiment, the present disclosure to provides a method of providing information for diagnosis of liver metastasis of colorectal cancer by measuring the mRNA expression level of CCL7 (Chemokine (C-C motif) ligand 7) gene or the expression level of CCL7 protein.

In yet another embodiment, the present disclosure provides a method for inhibiting metastasis of colorectal cancer in a patient suspected of having metastasis of colorectal cancer comprising administering to the patient a composition comprising an effective amount of an inhibitor of CCL7 or the CCL7 signaling pathway.

The present disclosure provides a composition for diagnosis of liver metastasis of colorectal cancer, which comprises a substance for measuring the mRNA level of CCL7 (Chemokine (C-C motif) ligand 7) gene or a substance for measuring the level of a protein which is encoded by the gene.

The present disclosure also provides a kit for diagnosis of liver metastasis of colorectal cancer, which comprises said composition for diagnosis of liver metastasis of colorectal cancer.

The present disclosure also provides a composition for inhibiting liver metastasis of colorectal cancer, which comprises an inhibitor of CCL7 (Chemokine (C-C motif) ligand 7) gene or the CCL7 signaling pathway.

The present disclosure also provides a method for providing information for diagnosis of liver metastasis of colorectal cancer, the method comprising the steps of: (a) measuring the mRNA level of CCL7 gene in a biological sample isolated from a patient suspected to have liver metastasis of colorectal cancer; and (b) comparing the measured mRNA level of CCL7 gene with the mRNA level of CCL7 gene in a control sample obtained from primary colorectal cancer tissue.

The present disclosure also provides a method for providing information for diagnosis of liver metastasis of colorectal cancer, the method comprising the steps of: (a)

measuring the level of CCL7 protein in a biological sample isolated from a patient suspected to have liver metastasis of colorectal cancer; and (b) comparing the measured protein level with the level of CCL7 protein in a control sample obtained from primary colorectal cancer tissue.

According to the present disclosure, whether liver metastasis of colorectal cancer occurred or not can be diagnosed by measuring the mRNA level of CCL7 gene or the expression level of CCL7 protein. In addition, the use of the composition comprising the inhibitor against CCL7 gene allows the treatment of colorectal cancer or the inhibition of liver metastasis of colorectal cancer.

DETAILED DESCRIPTION

Figure 1:
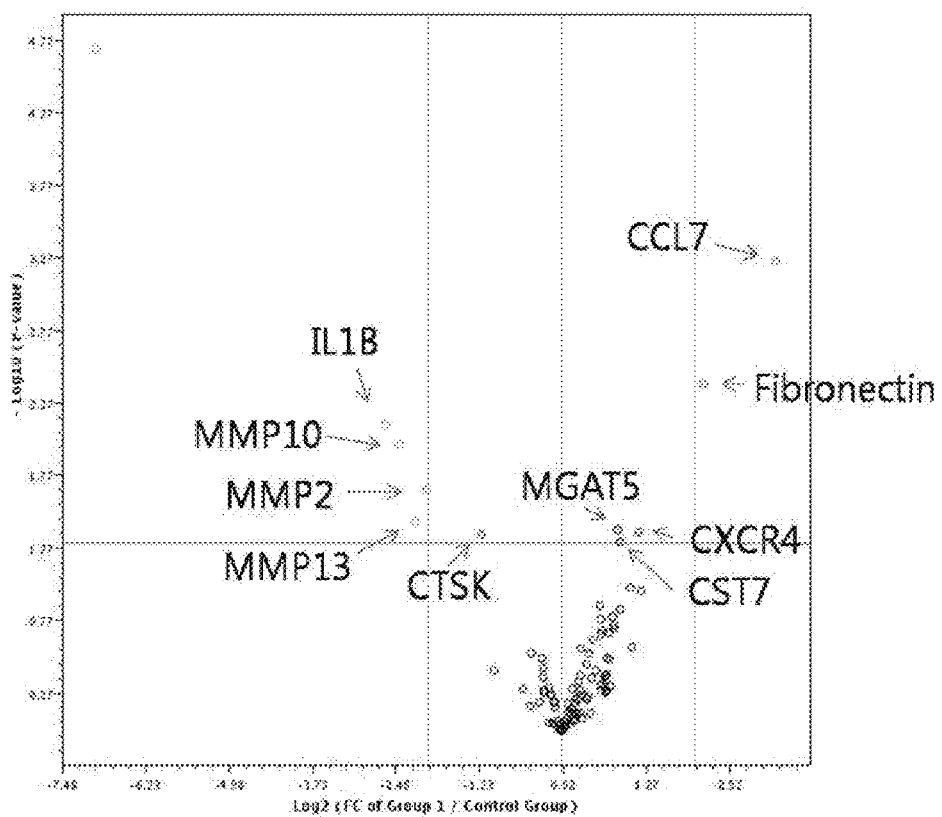
FIG. 1 shows the results of analysis of target genes showing a significant difference in gene expression between primary colorectal cancer and liver-metastasized colorectal cancer.

Unless defined otherwise, all technical and scientific terms used herein have the same meaning as commonly understood by one of ordinary skill in the art to which the invention pertains. Generally, the nomenclature used herein is one which is well known and commonly employed in the art.

The present inventors used an $RT^2$ Profiler PCR array to discover a biomarker associated with liver metastasis of colorectal cancer. The Profiler PCR array comprises a 96-well plate containing SYBR Green-optimized primer sets for genes, classified according to pathway (e.g., apoptosis, cell cycle, cancer, signal pathway, etc.) or disease, and allows the expressions of genes in a specific signal pathway to be analyzed at the same time using a real-time PCR-based technique.

CCL7 (Chemokine (C-C motif) ligand 7) discovered as a marker of liver metastasis of colorectal cancer in the present disclosure is a small chemokine which was previously called "monocyte-specific chemokine 3" (MCP-3). CCL7 has two adjacent N-terminal cysteine residues and serves to attract monocytes and to control the function of macrophages. Such CCL7 is known to be secreted from monocytes, fibroblasts, platelets, colonic epithelial cells and some malignant tumor cells and acts as a lymphocyte chemoattractant by binding to chemokine receptors (CCR1, CCR2, CCR3, and CCR5).

In one aspect, the present disclosure is directed to a composition for diagnosis of liver metastasis of colorectal cancer, which comprises a substance for measuring the mRNA level of CCL7 (Chemokine (C-C motif) ligand 7) gene or a substance for measuring the level of a protein which is encoded by the gene.

In the present disclosure, the substance for measuring the mRNA level of CCL7 gene is preferably a probe having a complementary sequence, specific for the CCL7 gene, and the use of the probe specific for the gene allows to be effectively detected at the mRNA level.

As used herein, the term "probe" means a nucleic acid fragment such as RNA or DNA, which can specifically bind to mRNA and has a length of several bases to several hundred bases. The probe is labeled so that the presence or absence of a specific mRNA can be determined. The probe can be constructed in the form of an oligonucleotide probe, a single stranded DNA probe, a double stranded DNA probe, an RNA probe or the like.

In the present disclosure, the substance capable of measuring the expression level of the protein which is encoded by the CCL7 gene may be an antibody or a fragment thereof, which binds specifically to the CCL7 protein. Herein, the antibody is intended to include all polyclonal antibodies, monoclonal antibodies and recombinant antibodies and means a specific molecular molecule directed toward antigenic sites.

A polyclonal antibody which is the liver disease marker protein can be produced by a method well known in the art, which includes injecting TM4SF5 antigen into an animal and collecting blood from the animal to obtain serum containing antibodies. This polyclonal antibody can be prepared from any animal host, such as goats, rabbits, sheep, monkeys, horses, pigs, cows and dogs. A monoclonal antibody can be prepared by a method well known in the art, such as a hybridoma method (see Kohler and Milstein (1976) European Journal of Immunology 6:511-519) or a phage antibody library technique (Clackson et al, Nature, 352:624-628, 1991; Marks et al, J. Mol. Biol., 222:58, 1-597, 1991). The antibody prepared by the above methods may be isolated using gel electrophoresis, dialysis, salting out, ion exchange chromatography, affinity chromatography, etc. In addition, the antibody of the present disclosure includes functional fragments of antibody molecules, as well as a complete form having two full-length light chains and two full-length heavy chains. The functional fragment of antibody molecules means a fragment having at least an antigen-binding function, and examples thereof Fab, F(ab')2, Fv, and the like.

In another aspect, the present disclosure is also directed to a kit for diagnosis of liver metastasis of colorectal cancer, which comprises said composition for diagnosis of liver metastasis of colorectal cancer.

The diagnostic kit of the present disclosure is composed of one or more compositions, solutions or instruments, which are suitable for analysis methods. It may be a RT-PCR kit, a DNA chip kit or a protein chip kit. The RT-PCR kit may comprise, in addition to each primer pair specific for the marker gene, a test tube or another suitable container, a reaction buffer, deoxynucleotides (dNTPs), enzymes such as Taq-polymerase, reverse transcriptase and DNase, an RNase inhibitor, DEPC-water, sterile water, etc. Also, it may comprise a primer pair specific for a gene which is used as a quantitative control. The DNA chip kit may comprise a substrate, a gene or corresponding cDNA attached as a probe to the substrate, and optionally a quantification control gene or corresponding cDNA attached to the substrate.

In addition, the diagnostic kit according to the present disclosure may comprise an agent for measuring the level of CCL7, in which the agent for measuring the protein is preferably an antibody specific for the protein. Thus, the diagnostic kit comprising the agent for measuring the protein level may be a kit for detection of diagnostic markers, which comprises essential elements required for carrying out, for example, ELISA. This kit may also comprise reagents that may detect bound antibodies, for example, labeled secondary antibodies, chromophores, enzymes (e.g., conjugated with antibodies) and their substrates. Also, it may comprise an antibody specific for a control protein for quantification.

Further, the amount of antigen-antibody complexes formed may be quantitatively determined by measuring the signal intensity of a detection label. Such a detection label may be selected from the group consisting of, but not limited to, enzymes, fluorescent substances, ligands, luminescent substances, microparticles, redox molecules and radioactive isotopes. Methods for measuring protein levels include, but not limited to, Western blotting, ELISA (enzyme linked immunosorbent assay), immunohistostaining, FACS and protein chip assays.

In still another aspect, the present disclosure is also directed to a composition for inhibiting liver metastasis of colorectal cancer, which comprises an inhibitor of CCL7 (Chemokine (C-C motif) ligand 7) or the CCL7 signaling pathway.

The inhibitor against the CCL7 (Chemokine (C-C motif) ligand 7) gene may be an antisense oligonucleotide against the mRNA of the CCL7 gene, or it may be a siRNA of the CCL7 gene. The siRNA may be one of the following sequences:

```
CCL7 siRNA #1
sense:
                                    (SEQ ID NO: 11)
5'-GAACAUUCAUGACUGAACU-3' antisense:
                                    (SEQ ID NO: 12)
5'-AGUUCAGUCAUGAAUGUUC-3'

CCL7 siRNA #2
sense:
                                    (SEQ ID NO: 13)
5'-CUGAACUAAAAACAAGCCA-3' antisense:
                                    (SEQ ID NO: 14)
5'-UGGCUUGUUUUUAGUUCAG-3'.
```

The inhibitor of the CCL7 signaling pathway may be an antibody, or combination of antibodies, which bind to and neutralize CCL7, or otherwise block the ability of CCL7 to bind to CCR3. The antibody may be monoclonal, polyclonal, or recombinant.

The inhibitor of the CCL7 signaling pathway may be a pharmacological agent, including, but not excluding, small molecule pharmacological agents. A non-limiting example of a pharmacological inhibitor of the CCL7 signaling pathway is an antagonist of CCR3. SB328437, AZD3778, and Ki19003 are non-limiting examples of CCR3 antagonists As used herein, the term "siRNA" (small interfering RNA) means a short double-strand RNA (dsRNA) that mediates efficient gene silencing in a sequence-specific manner. SiRNAs has the potential to be a very potent drug for the inhibition of specific gene expression in vivo in light of its long-lasting effectiveness in cell cultures and in vivo, its ability to transfect cells in vivo, and its resistance to degradation in serum. siRNA can exhibit effects equal or higher than those of antisense oligonucleotides even at relatively low concentrations, and thus has been proposed as an alternative for antisense oligonucleotides. A person skilled in the art can synthesize and modify the antisense oligonucleotide and siRNA in a desired manner using a method known in the art.

In yet another aspect, the present disclosure is also directed to a method for providing information for diagnosis of liver metastasis of colorectal cancer, the method comprising the steps of: (a) measuring the mRNA level of CCL7 gene in a biological sample isolated from a patient suspected to have liver metastasis of colorectal cancer; and (b) comparing the measured mRNA level of CCL7 gene with the mRNA level of CCL7 gene in a control sample obtained from primary colorectal cancer tissue.

In a further aspect, the present disclosure is also directed to a method for providing information for diagnosis of liver metastasis of colorectal cancer, the method comprising the steps of: (a) measuring the level of CCL7 protein in a biological sample isolated from a patient suspected to have liver metastasis of colorectal cancer; and (b) comparing the measured level of CCL7 protein with the level of CCL7 protein in a control sample obtained from primary colorectal cancer tissue.

In another aspect, the present disclosure is directed to a method for inhibiting metastasis of colorectal cancer in a patient comprising administering to the patient a composition comprising an effective amount of an inhibitor of CCL7 or an inhibitor the CCL7 signaling pathway, wherein the metastasized colorectal cancer tissue from the patient has an increased level of CCL7 mRNA compared to the level of CCL7 mRNA in the primary colorectal cancer tissue. The CCL7 inhibitor or CCL7 signaling pathway inhibitor may be administered following resection surgery of the primary colorectal cancer. The patient may have, or be suspected of having, metastasis of colorectal cancer. The level of CCL7 can be determined by obtaining mRNA from samples of primary colorectal cancer and colorectal cancer which has metastasized to another location of the body and measuring the level of CCL7 mRNA in the primary and metastasized colorectal cancer samples. The CCL7 mRNA may be measured via conventional means known in the art, such as via qualitative RT-PCR.

In the present disclosure, the step of measuring the level of CCL7 protein in the biological sample isolated from the patient suspected to have liver metastasis of colorectal cancer can be performed by brining the inventive composition for diagnosis of liver metastasis of colorectal cancer into contact with the biological sample. Also, the step of comparing the measured protein level with the level of CCL7 protein in a control sample obtained from primary colorectal tissue includes determining whether the level of CCL7 protein in the sample is higher that of CCL7 in the control sample, thereby providing information for diagnosis of liver metastasis of colorectal cancer.

According to such methods of the present disclosure, by comparing the expression level of CCL7 protein in the primary colorectal cancer control sample with the expression level of CCL7 protein in the sample isolated from the patient suspected to have liver metastasis of colorectal cancer, a patient having liver metastasis of colorectal cancer can be diagnosed and, furthermore, the progression or prognosis of colorectal cancer can be predicted.

In the present disclosure, the step of measuring the level of CCL7 protein can be performed by measuring the level of CCL7 protein using an antibody that specifically recognizes CCL7. Specifically, the step can be performed using the above-mentioned various methods of measuring protein levels, including Western blotting, ELISA (enzyme linked immunosorbent assay), FACS, and protein chip assays.

In the present disclosure, the biological sample may be tissue, cell, whole blood, serum or plasma.

Hereinafter, the present invention will be described in further detail with reference to examples. It will be obvious to those skilled in the art that these examples are illustrative purposes only and are not to be construed to limit the scope of the present invention.

EXAMPLES

Example 1. Discovery of Gene Specific for Liver Metastasis of Colorectal Cancer

To analyze target genes showing a significant difference in gene expression between primary colorectal cancer and liver-metastasized colorectal cancer, RNA was extracted from the colorectal cancer tissue and liver-metastasized colorectal cancer tissue (fresh frozen tissue) of six patient (Samsung Medical Center, Korea), who had liver metastasis of colorectal cancer and underwent surgery (colorectal and liver resection). The extracted RNA was subjected to $RT^2$ Profiler PCR Array analysis.

Specifically, the colorectal cancer tissue and liver-metastasized colorectal cancer tissue of the six patients were frozen at −80° C. until use. The frozen tissues were stained with H&E, and necrotic tumor tissues and intervening normal tissues were removed therefrom. Then, the total RNA was extracted from the frozen tissues using a Nucleospin RNA kit. cDNA was synthesized from the extracted RNA using a $RT^2$ First Strand Synthesis Kit (Super Array Bioscience, Frederick, Md.) and analyzed using a Human tumor metastasis PCR array and a $RT^2$ SYBR Green/Rox PCR mastermix [APMM012C and PA-012-24, (Super Array Bioscience, Frederick, Md.)].

As a result, it was found that the expressions of CCL7 (p=0.0006), FN1 (p=0.0039), CXCR4 (p=0.0420), CST7 (p=0.0491) and MGAT5 (p=0.0407) were higher in the liver-metastasized colorectal cancer tissue than in the primary colorectal cancer tissue, and among them CCL7 (p=0.0006) showed the highest expression level (see FIG. 1).

Example 2-1: mRNA Expression Level of CCL7 Gene in Liver-Metastasized Colorectal Cancer Tissue In order to examine whether the CCL7 gene which showed an expression level higher in the liver-metastasized colorectal cancer tissue than in the primary colorectal cancer tissue as described in Example 1 functions as a marker of liver metastasis of colorectal cancer, the following experiment was carried out.

Total RNA was extracted from paraffin blocks using the MasterPure™ Complete DNA and RNA Purification Kit (Epicentre Biotechnologies). mRNA was amplified and then transcribed from double-stranded cDNA using Super-Script™ III Reverse transciptase (Invitrogen). Quantitative real-time RT PCR of the mRNA was performed three times in a 384-well plate. Each PCR reaction was performed 5 µL of Power SYBR®Green PCR Master Mix (Applied Biosystems, Inc., Foster City, Calif.), 0.25 µL of 10 µM primer, and a probe set of CCL7 (Bioneer Oligo Synthesis Report), CCR1 (Bioneer Oligo Synthesis Report), CCR2 (Bioneer Oligo Synthesis Report), CCR3 (Bioneer Oligo Synthesis Report) and GAPDH (Bioneer Oligo Synthesis Report). The primer sets used in the PCR reactions are shown in Table 1 below.

TABLE 1

| Marker | | sequence | SEQ ID NO |
|---|---|---|---|
| CCL7 | Sense | 5'-TGCTCAGCCAGTTGGGATTA-3' | 1 |
|  | antisense | 5'-GGACAGTGGCTACTGGTGGT'3' | 2 |
| CCR1 | Sense | 5'-CTGGTTGGAAACATCCTGGT-3' | 3 |
|  | antisense | 5'-GGAAGCGTGAACAGGAAGAG-3' | 4 |
| CCR2 | Sense | 5'-CCCCAGTCACCTGCTGTTAT-3' | 5 |
|  | antisense | 5'-GCTTCTTTGGGACACTTGCT-3' | 6 |
| CCR3 | Sense | 5'-GTGTTCACTGTGGGCCTCTT-3' | 7 |
|  | antisense | 5'-GTGACGAGGAAGAGCAGGTC-3' | 8 |
| GAPDH | Sense | 5'-ACCGTCAAGGCTGAGAA-3' | 9 |
|  | antisense | 5'-CATCGCCCCACTTGATT-3' | 10 |

Figure 2A:
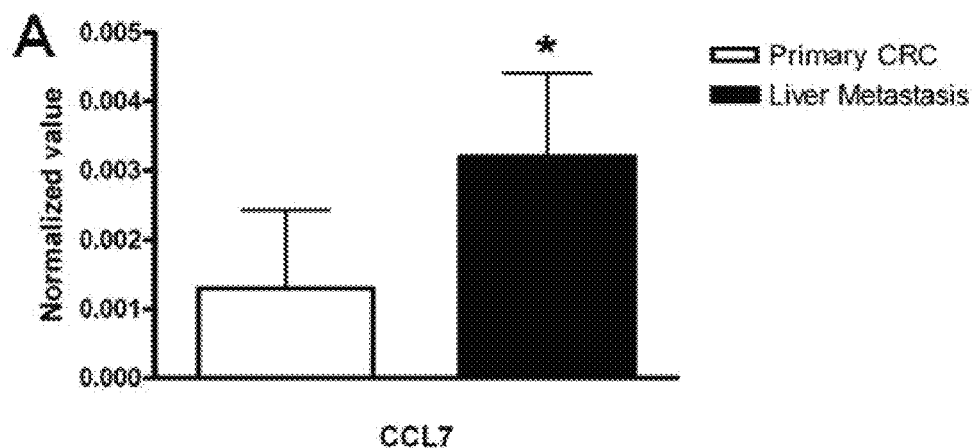
FIGS. 2A and 2B show a comparison of the expression of CCL7 between the primary site of colorectal cancer and the liver metastasis tissue of colorectal cancer, and a comparison of the expression of the CCL7 receptors CCR1, CCR2 and CCR3 between the primary site of colorectal cancer and the liver metastasis tissue of colorectal cancer.
Figure 2B:
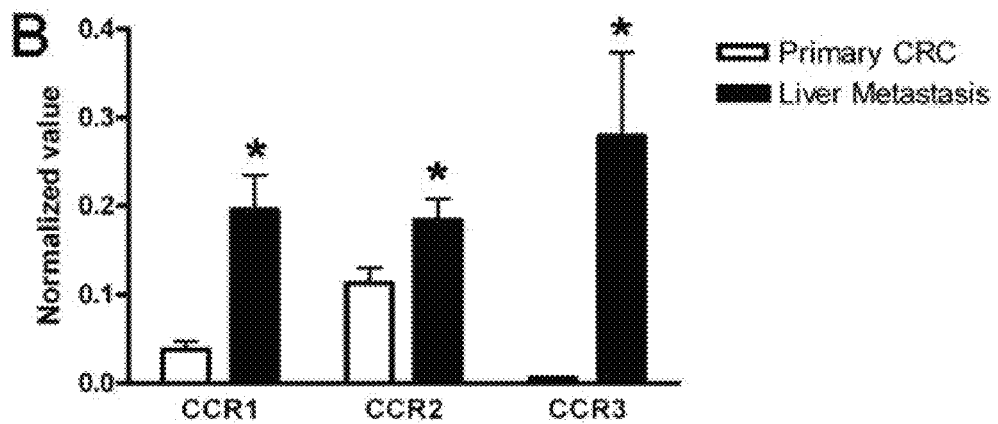

$RT^2$ Profiler PCR Array and real time PCR were performed on the primary colorectal cancer tissue and the liver-metastasized colorectal cancer tissue. As a result, the RNA expression of CCL7 was higher in the liver-metastasized colorectal cancer tissue than in the primary colorectal cancer tissue (FIG. 2A). Also, CCR1, CCR2 and CCR3 known as CCL7 receptors also showed RNA expression levels higher in the liver-metastasized colorectal cancer tissue than in the primary colorectal cancer tissue (see FIG. 2B).

Figure 3A:
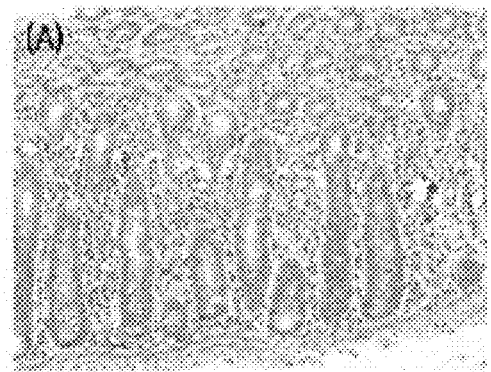
FIGS. 3A, 3B, and 3C are photographs of immunohistochemical staining of CCL7 in normal colorectal tissue (H&E, ×200), immunohistochemical staining of CCL7 in primary colorectal cancer tissue (H&E, ×200), immunohistochemical staining of CCL7 in the liver metastasis tissue of colorectal cancer (H&E, ×200).
Figure 3B:
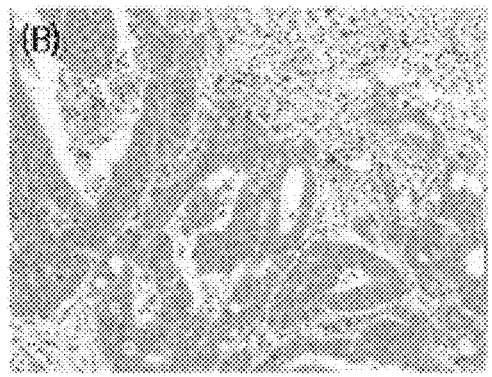
Figure 3C:

Example 2-2: Expression Level of CCL7 Protein in Liver-Metastasized Colorectal Cancer Tissue Immunohistochemical staining was performed using an antibody (rabbit anti-human polyclonal CCL7 (dilution 1:1000, GenWay Biotech, Inc., USA) against CCL7. As a result, although CCL7 was also expressed in normal colorectal tissue, the colorectal cancer tissue (see FIG. 3B) showed a strong expression of CCL7 as compared to the normal colorectal tissue (see FIG. 3A), and the liver-metastasized colorectal cancer tissue (see FIG. 3C) showed a strong expression of CCL7 as compared to the primary colorectal cancer tissue (see FIG. 3). It could be seen from such results that CCL7 is highly valuable as a marker specific for liver metastasis of colorectal cancer. If CCL7 acts as a marker specific for liver metastasis of colorectal cancer, an antibody targeting CCL7 can be developed and used as a targeted agent.

Example 3: CCL7 Increases Expression of the Chemokine Receptor CCR3

In order to determine the effect of CCL7 on CCR3 expression, HCT116 colorectal cancer cells were stably transfected with GFP (control) or CCL7. CCR1, CCR2, CCR3, CCR5, and CCL7 levels were determined by Western blot and FACS analyses.

For the Western blot, lysates from transfected HCT116 cells were obtained using Pro-prep buffer (Intron Biotechnology, Seoul, Korea), including protease inhibitors. 20-60 µg the protein extract was resolved by SDS-PAGE and transferred to polyvinylidene fluoride (PVDF) membranes and probed with antibodies against CCR1, CCR2, CCR3, CCR5, CCL7, and β-actin, as a loading control. Secondary antibodies conjugated to horseradish peroxidase were used to image the membrane.

For the flow cytometry, HCT116 colorectal cancer cells were incubated with 200 ng/mL recombinant CCL7 for up to 12 hours. Following incubation, the cells were washed, blocked, and then stained with anti-human antibodies against CCR1, CCR2, CCR3, or CCR5 followed by staining with a PE-conjugated secondary antibody.

Figure 4A:
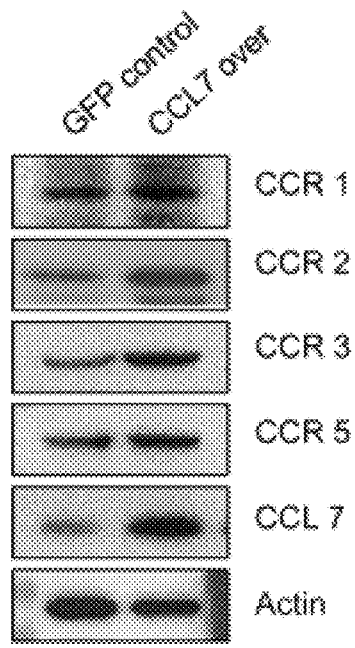
FIGS. 4A and 4B show a Western blot of lysates of HCT116 colorectal cancer cells expressing GFP or overexpressing CCL7, and FACS analysis of HCT116 treated with CCL7 recombinant protein.
Figure 4B:
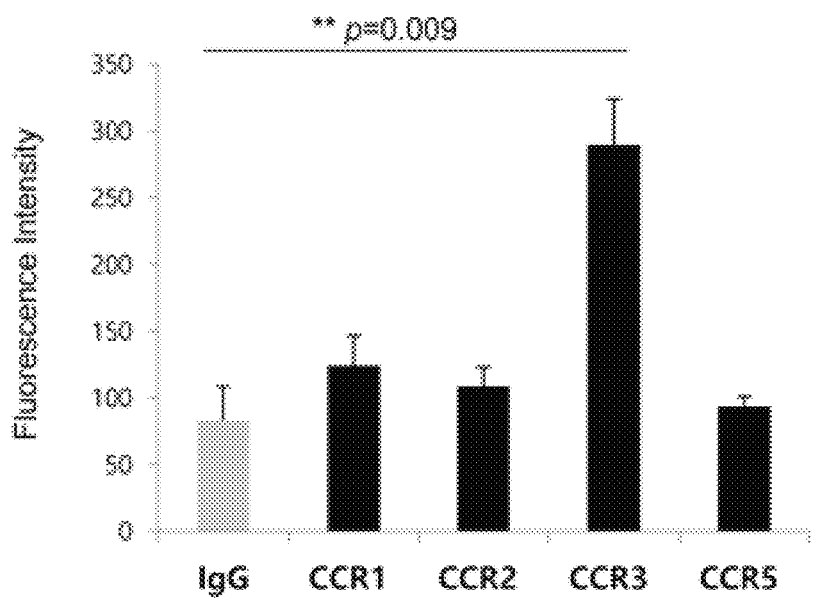

Overexpression of CCL7 in colorectal cancer cells significantly and dramatically increased protein expression of CCR3 compared with GFP controls (FIGS. 4A and 4B).

Example 4: CCL7 Induces Loss of E-Cadherin and Promotes Expression of N-Cadherin and Vimentin Downregulation of E-cadherin and increased expression of N-cadherin and vimentin on cell membranes enables cancer cell migration and invasion into target tissue (e.g., the liver). To explore the function of CCL7 in colon cancer motility and invasiveness, the effect of CCL7 on expression of E-cadherin, N-cadherin, and was explored.

HCT116 colorectal cancer cells were incubated in the presence or absence of recombinant CCL7 for 1, 3, 6, or 12 hours. These cells were stained for E-cadherin and analyzed via FACS analysis.

HCT116 colorectal cancer cells were also stably transfected with GFP (control) or CCL7 and protein expression of E-cadherin, N-cadherin, vimentin, and β-actin, as a loading control, was determined by Western blot analysis.

HCT116 colorectal cancer cells were transfected with siRNA to lower expression of the CCL7 gene, and protein expression of CCL7, E-cadherin, Snail, vimentin, twist, and β-actin, as a loading control, was determined by Western blot analysis.

HCT116 colorectal cancer cells were also treated with anti-CCL7 antibodies and the CCR3 expression in cell extracts was determined via Western blot analysis.

HCT116 colorectal cancer cells were stably transfected with GFP (control) or CCL7 and the expression of E-cadherin, α-SMA, vimentin, twist, and β-actin, as a loading control, was determined via Western blot analysis.

Figure 5A:
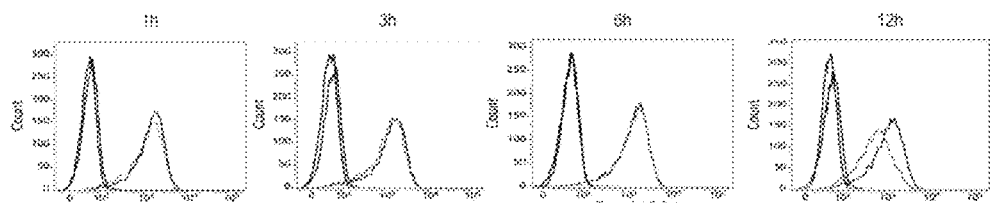
FIGS. 5A, 5B, 5C and 5D show the time-expression of E-cadhedrin in HCT116 cells treated with recombinant CCL7 for 1, 3, 6, and 12 hours, Western blots of HCT116 cells stably transfected with GFP or CCL7, or HCT116 cells transiently transfected with control or CCL7-specific siRNA, Western blots of extracts from HCT116 cells treated with control or anti-CCL7 antibodies, and expression of EMT markers in HCT116 cells stably transfected with GFP or CCL7, with or without treatment of SB328437, a CCR3 antagonist.
Figure 5B:
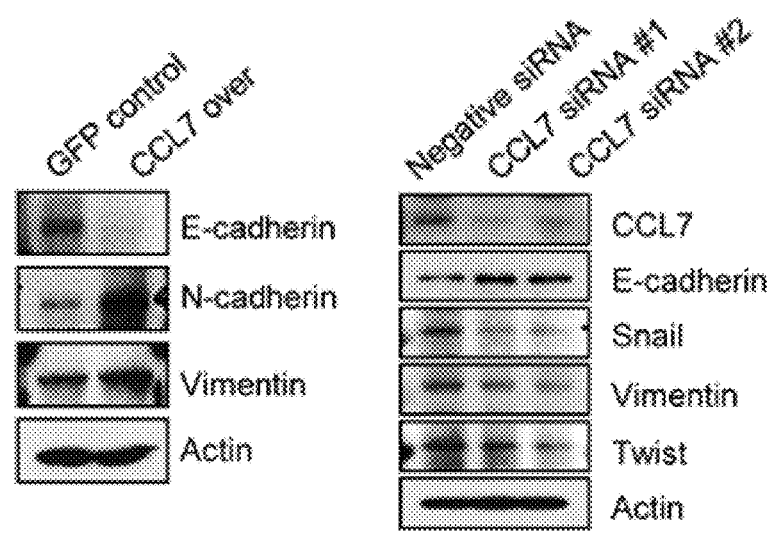

Overexpression of CCL7 induced the loss of E-cadherin and promoted expression of N-cadherin. Shifting the E-cadherin/N-cadherin balance towards N-cadherin promotes migration and invasion of colorectal cancer cells. Furthermore, reducing CCL7 expression in HCT116 colorectal cancer cells with siRNA increased E-cadherin expression, and reduced master EMT transcription factors snail, twist, and vimentin (FIG. 5B).

Figure 5C:
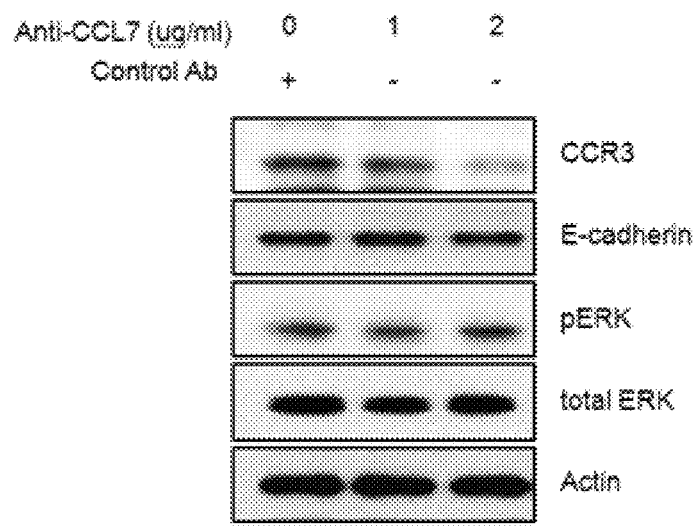

Blocking CCL7 signaling with an anti-CCL7 antibody produced results similar to the effect of reduced CCL7 expression due to siRNA. When CCL7 is neutralized by anti-CCL7 antibodies, CCR3 expression is markedly reduced with no change in expression of E-cadherin (FIG. 5C).

Figure 5D:
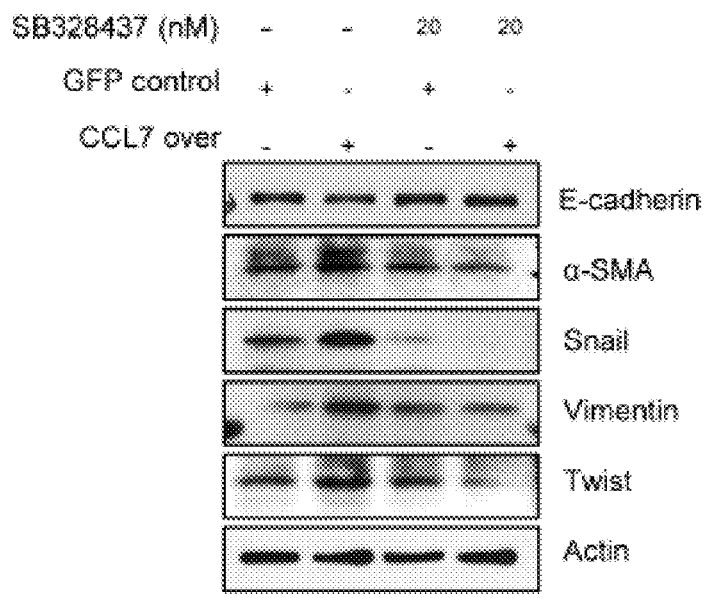

The effect of CCL7 on E-cadherin is also blocked by inhibiting the CCL7 signaling pathway with SB328437, a CCR3 antagonist. Overexpression of CCL7 reduced E-cadherin and increased expression of α-SMA, vimentin, and twist. This effect is blocked by the presence of SB328437 (FIG. 5D). These results provide a *nexus* between CCL7 expression, signaling through CCR3, and the resulting effect on E-cadherin, N-cadherin, vimentin, snail, and twist. The results demonstrated in FIGS. 4 and 5 show that CCL7 downregulates E-cadherin, and promotes expression of N-cadherin, vimentin, snail, and twist. This combination suggests that the CCL7 promotes migration and invasion of target tissues by colorectal cancer cells.

Example 5: CCL7 Induces Migration and Invasion of Colon Cancer Cells Via CCR3

To explore the role of CCL7 on migration and invasion of cancer cells, HCT116 colorectal cancer cells were transiently transfected with siRNA to the CCL7 gene or stably transfected with GFP (control) or CCL7. The cells ($5 \times 10^4$) were loaded into the migration and invasion chambers in a 24-well plate in serum-free RPMI media. The lower chambers were supplemented with 10% FBS and the cells were incubated for 24 or 48 hours. The cells were stained with calcein or hematoxylin-eosin and mounted. Cell migration and invasion was quantified via fluorescence.

Figure 6A:
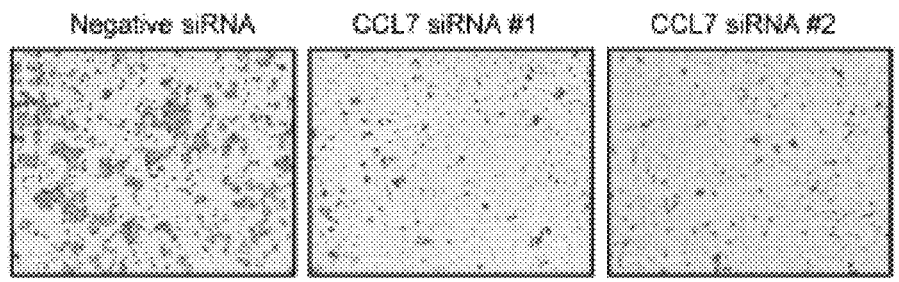
FIGS. 6A, 6B and 6C show a transwell matrigel invasion assay of HCT116 cells after stable transfection with control or CCL7 siRNA, cell migration (top) and invasion (bottom) assays using a transwell migration chamber of HCT116 cells after stable transfection with GFP or CCL7, and invasion of HCT116 cells expressing GFP or CCL7 in the presence or absence of SB328437.

As expected, knockdown of CCL7 with siRNA against the CCL7 gene inhibits invasion of HCT116 colorectal cancer cells (FIG. 6A).

Figure 6B:
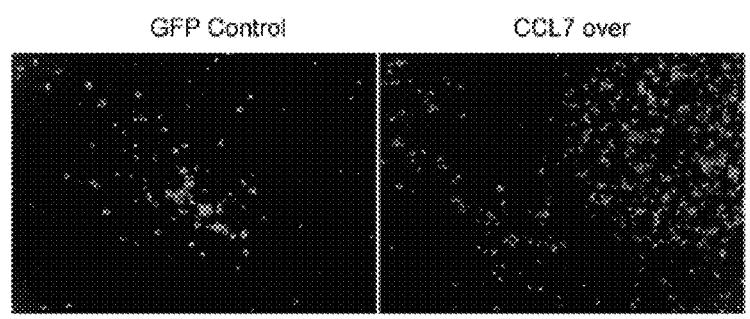
Figure 6B:
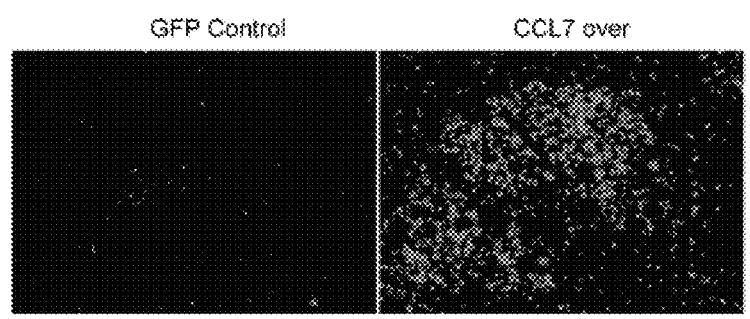
Figure 6C:
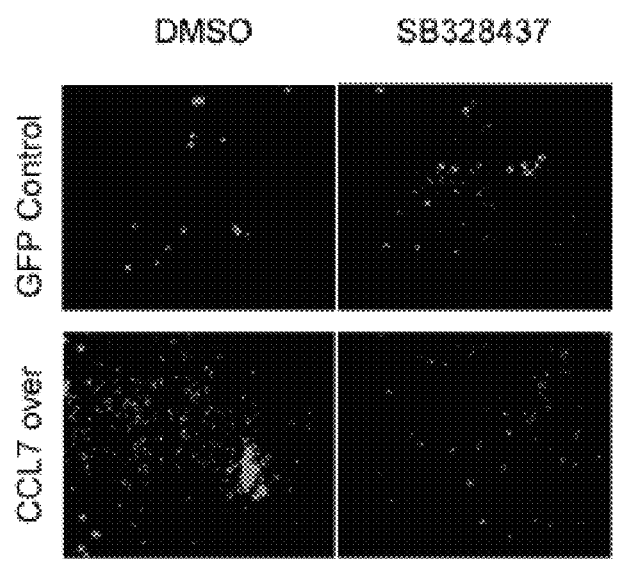

Trans-well migration chamber analysis show that the migration and invasion abilities of CCL7 overexpressing cells were increased more than 2-fold compared to those of control (FIG. 6B). GFP and CCL7 transfected HCT116 were treated with SB328437. The presence of a CCR3 antagonist blocked the CCL7-induced migration and invasion of the colorectal cancer cells. (FIG. 6C).

Example 6: CCL7 Signaling Activates ERK and JNK

To explore the role of CCL7 signaling and CCR3 in the EMT-related pathway, activation of ERK and JNK was measured. HCT116 colorectal cancer cells were transiently transfected with siRNA against CCL7 or stably transfected with GFP (control) or CCL7. The stably transfected cells were incubated in the presence or absence of 20 µM SB328437. Cell lysates were obtained as above and assayed via Western blot analysis for pERK, total ERK, pJNK, total JNK, and β-actin.

Figure 7A:
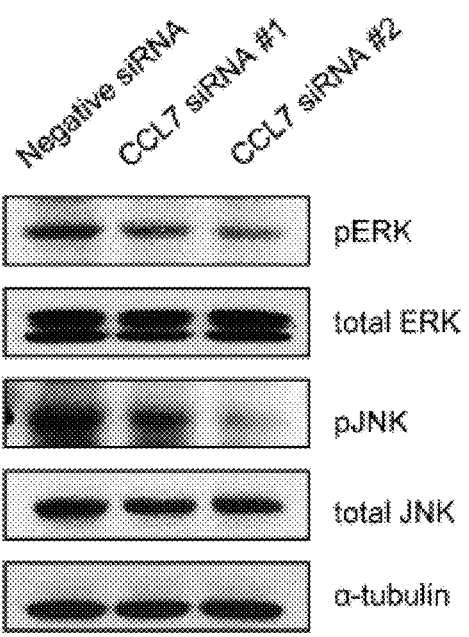
FIGS. 7A and 7B show activation markers of the ERK/JNK pathways in HCT116 cells transiently transfected with control or CCL7 siRNA, and activation markers of the ERK/JNK pathways in HCT116 cells stably transfected with GFP or CCL7 in the presence or absence of SB328437.
Figure 7B:
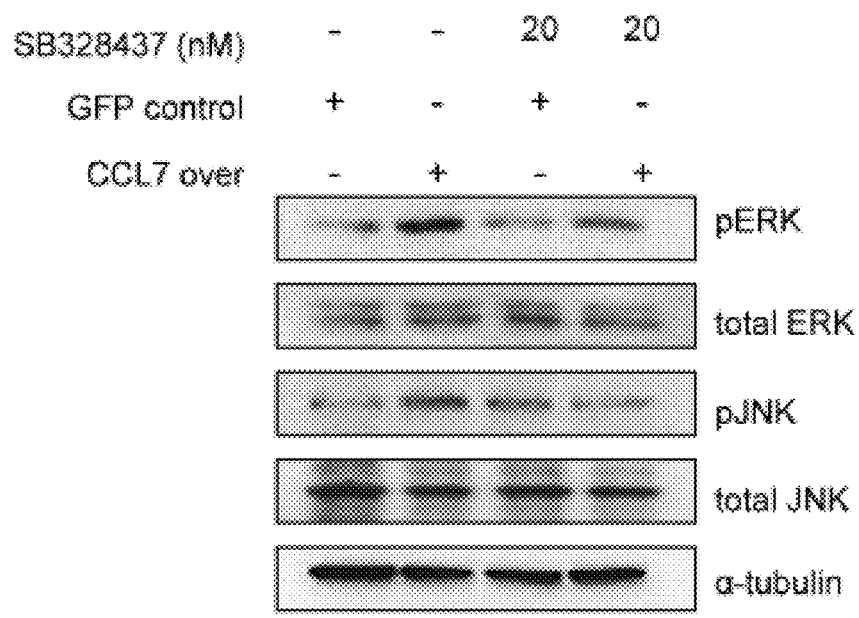

Western blot analysis confirmed that CCL7 correlated with ERK and JNK activation. Knockdown of CCL7 with siRNA reduced activation of both ERK and JNK, indicating that the EMT pathway is activated by CCL7 (FIG. 7A). Furthermore, phosphorylation of ERK and JNK were increased by CCL7 overexpression. This effect was inhibited by the presence of SB328437 (FIG. 7B).

Example 7: CCL7 Overexpression Promotes Tumorigenicity and Metastasis of HCT116 Colorectal Cells In Vivo The in vitro data above suggest that CCL7 induces changes to colorectal cancer cells which enhance migration and invasion of tissues (e.g., liver). To confirm these in vitro findings, HCT116 colorectal cancer cells stably transfected with GFP (control) or CCL7 were transplanted into nude mice. Control or CCL7 overexpressing HCT116 cells were suspended in 50 mL PBS with 50% matrigel and injected subcutaneously into the flanks of 6-week old female BALB/c nu/nu mice. Tumor size was measured once a week with a caliper and tumor size was calculated with the following formula: (short length×long length×width)/2.

Figure 8A:
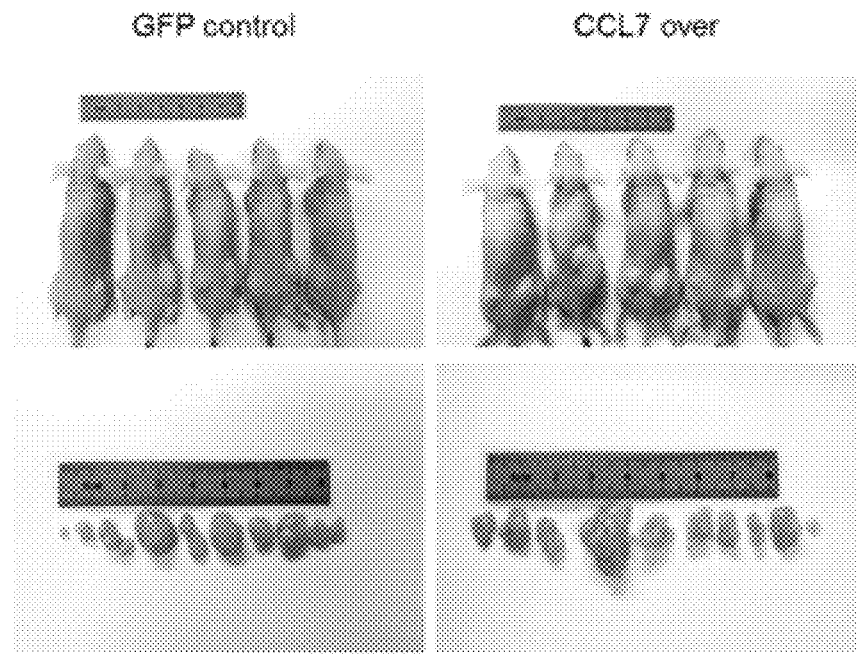
FIGS. 8A and 8B show images of mice with tumors and the tumors themselves 3 weeks after transplantation of HCT116 expressing GFP (control) or CCL7, and displays mean tumor volume of tumors in mice following transplantation of HCT116 cells expressing GFP or overexpressing CCL7.
Figure 8B:
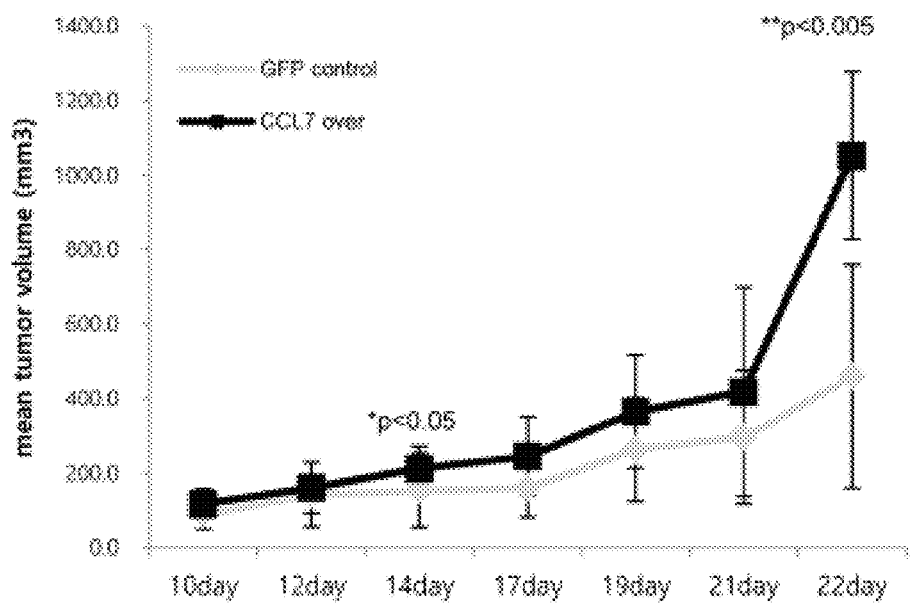

HCT116 cancer cells overexpressing CCL7 promoted significantly larger tumors than control HCT116 cancer cells (FIGS. 8A and B). Further, when GFP- or CCL7-expressing HCT116 colorectal cancer cells were transplanted to the cecum of nude mice, 80% of the mice receiving the CCL7 overexpressing HCT116 colorectal cancer cells developed liver metastases and 60% developed lung metastases. None of the mice receiving control, GFP-transfected HCT116 colorectal cancer cells developed liver or lung metastases (Table 1)

| Group | Cell no. | Total Metastasis | Liver Metastasis | Lung Metastasis |
|---|---|---|---|---|
| HCT116 GFP | $10^6$ | 0/6 (0%) | 0/6 (0%) | 0/6 (0%) |
| HCT116 CCL7* | $10^6$ | 4/5 (80%) | 4/5 (80%) | 3/5 (60%) |

*One mouse died within 2 days of transplant and was excluded from analysis

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

Various embodiments of the present disclosure are further described below:

1. A composition for diagnosis of liver metastasis of colorectal cancer comprising a substance for measuring the mRNA level of CCL7 (Chemokine (C-C motif) ligand 7) gene or a substance for measuring the level of a protein which is encoded by the gene.
2. A composition for diagnosis of liver metastasis of colorectal cancer, wherein the substance for measuring the mRNA level of CCL7 is a probe having a complementary sequence specific for the CCL7.
3. A composition for diagnosis of liver metastasis of colorectal cancer, wherein the substance for measuring the level of CCL7 protein is an antibody or a fragment thereof that binds specifically to the protein which is encoded by the gene.
4. A kit for diagnosis of liver metastasis of colorectal cancer comprising a composition for diagnosis of liver metastasis of colorectal cancer.
5. A composition for inhibiting liver metastasis of colorectal cancer comprising an inhibitor of CCL7 (Chemokine (C-C motif) ligand 7) gene.
6. A composition for inhibiting liver metastasis of colorectal cancer, wherein the inhibitor against the CCL7 gene is an antisense oligonucleotide against the mRNA of the CCL7 gene.
7. The composition for inhibiting liver metastasis of colorectal cancer, wherein the inhibitor against the CCL7 gene is a siRNA of the CCL7 gene.
8. A method for providing information for diagnosis of liver metastasis of colorectal cancer comprising the steps of:
(a) measuring the mRNA level of CCL7 gene in a biological sample isolated from a patient suspected to have liver metastasis of colorectal cancer; and
(b) comparing the measured mRNA level of CCL7 gene with the mRNA level of CCL7 gene in a control sample obtained from primary colorectal cancer tissue.
9. A method for providing information for diagnosis of liver metastasis of colorectal cancer comprising the steps of:
(a) measuring the level of CCL7 protein in a biological sample isolated from a patient suspected to have liver metastasis of colorectal cancer; and
(b) comparing the measured protein level of with the level of CCL7 protein in a control sample obtained from primary colorectal cancer tissue.

SEQUENCE LISTING

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A method of inhibiting metastasis of colorectal cancer in a patient with primary colorectal cancer, comprising:
   administering to the patient a therapeutically effective amount of an active agent selected from the group consisting of a siRNA of the CCL7 gene and an anti-CCL7 antibody,
   wherein the siRNA is a combination of SEQ ID NOs:13 and 14.

2. The method of claim 1, wherein the active agent is a siRNA of the CCL7 gene.

3. The method of claim 1, wherein the active agent is an anti-CCL7 antibody.

4. The method of claim 1, wherein the primary colorectal cancer has been resected.

5. The method of claim 4, wherein the primary colorectal cancer has been resected prior to administration of the active agent.

* * * * *

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
tgctcagcca gttgggatta                                          20

```
<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ggacagtggc tactggtggt                                                   20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
ctggttggaa acatcctggt                                                   20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ggaagcgtga acaggaagag                                                   20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ccccagtcac ctgctgttat                                                   20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gcttctttgg gacacttgct                                                   20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gtgttcactg tgggcctctt                                                   20

<210> SEQ ID NO 8
<211> LENGTH: 20
<212> TYPE: DNA
<213> ORGANISM: Artificial Sequence
<220> FEATURE:
<223> OTHER INFORMATION: primer
```

-continued

```
<400> SEQUENCE: 8
gtgacgagga agagcaggtc                                              20

<210> SEQ ID NO 9
<211> LENGTH: 17
<212> TYPE: DNA
<213> ORGANISM: Artificial Sequence
<220> FEATURE:
<223> OTHER INFORMATION: primer

<400> SEQUENCE: 9
accgtcaagg ctgagaa                                                 17

<210> SEQ ID NO 10
<211> LENGTH: 17
<212> TYPE: DNA
<213> ORGANISM: Artificial Sequence
<220> FEATURE:
<223> OTHER INFORMATION: primer

<400> SEQUENCE: 10
catcgcccca cttgatt                                                 17

<210> SEQ ID NO 11
<211> LENGTH: 19
<212> TYPE: RNA
<213> ORGANISM: Artificial Sequence
<220> FEATURE:
<223> OTHER INFORMATION: siRNA 1 sense

<400> SEQUENCE: 11
gaacauucau gacugaacu                                               19

<210> SEQ ID NO 12
<211> LENGTH: 19
<212> TYPE: RNA
<213> ORGANISM: Artificial Sequence
<220> FEATURE:
<223> OTHER INFORMATION: siRNA 1 antisense

<400> SEQUENCE: 12
aguucaguca ugaauguuc                                               19

<210> SEQ ID NO 13
<211> LENGTH: 19
<212> TYPE: RNA
<213> ORGANISM: Artificial Sequence
<220> FEATURE:
<223> OTHER INFORMATION: siRNA 2 sense

<400> SEQUENCE: 13
cugaacuaaa aacaagcca                                               19

<210> SEQ ID NO 14
<211> LENGTH: 19
<212> TYPE: RNA
<213> ORGANISM: Artificial Sequence
<220> FEATURE:
<223> OTHER INFORMATION: siRNA 2 antisense

<400> SEQUENCE: 14
uggcuuguuu uuaguucag                                               19
```